United States Patent [19]

Dietlin et al.

[11] Patent Number: 5,175,172
[45] Date of Patent: Dec. 29, 1992

[54] METHOD OF ALLEVIATING AIDS SYMPTOMS AND COMPOSITIONS THEREFOR

[76] Inventors: Francois Dietlin, 17 Rue du Marechal Foch, 78110 Le Vesinet; Daniele Fredj, 13 bis Chemin des Rougemonts, 91190 GIF S/Yvette, both of France

[21] Appl. No.: 541,047

[22] Filed: Jun. 20, 1990

Related U.S. Application Data

[63] Continuation-in-part of Ser. No. 451,757, Dec. 18, 1989, abandoned.

[30] Foreign Application Priority Data

Dec. 19, 1988 [FR] France ............................... 88 16749

[51] Int. Cl.⁵ .................. C07D 219/08; A61K 31/395
[52] U.S. Cl. ..................................... 514/297; 546/105
[58] Field of Search ........................ 546/105; 514/297

[56] References Cited

U.S. PATENT DOCUMENTS 4,851,536  7/1989  Skotnicki et al. .................. 546/105

FOREIGN PATENT DOCUMENTS 0306825  3/1989  European Pat. Off. .
0306826  3/1989  European Pat. Off. .

OTHER PUBLICATIONS

Chemical & Engineering News, vol. 67, No. 26, pp. 7-16 (1989).
R. Faure, J. Chim. Phys. Chim Biol. 78 (6) (1981) 527.
M. E. Konshin Khim, Pharm. Zhur. 5(11) (1971) 10-12.
S. K. Baveha, Ind. J. Pharm. Sci. 48 (1981) 23-25.

*Primary Examiner*—Nicholas S. Rizzo
*Attorney, Agent, or Firm*—Omri M. Behr; Matthew J. McDonald

[57] ABSTRACT

There are provided pharmaceutical compositions and methods of utilizing them for the elevation of $T_4$ lymphocytes levels in patients having subnormal levels thereof reducing the level of opportunistic infections in AIDS patients as well as, usually, $P_{24}$ levels and also for inhibiting the activity of the HIV virus in patients which are HIV seropositive but may not exhibit AIDS symptoms, which comprise, as active constituent an effective amount of a compound selected from the group consisting of 9-amino-1,2,3,4-tetrahydroacridine and the acid addition salts thereof with pharmaceutically acceptable acids. There are also provided, for the same purpose chemical derivatives of 9-amino-1,2,3,4-tetrahydroacridine which are capable of degradation by human stomach acids, other gastric fluids or intestinal enzymes to 9-amino-1,2,3,4-tetrahydroacridine and have the formula 9-N(Q)-1,2,3,4-tetrahydroacridine, wherein Q is <(A.B) where A and B are the same or different and are biologically labile groups. Further included are analogues of the foregoing compounds which carry a substituent in the homoaromatic ring.

9 Claims, No Drawings

METHOD OF ALLEVIATING AIDS SYMPTOMS AND COMPOSITIONS THEREFOR

RELATED APPLICATIONS

This application is a continuation-in-part of copending application Ser. No. 07/451,757, filed Dec. 18, 1989, now abandoned.

BACKGROUND OF THE INVENTION

1. Field of the Invention

Immunological therapy, in particular regeneration of $T_4$ lymphocytes and reduction of opportunistic infections in AIDS patients.

2. Discussion of the Prior Art

9-Amino-1,2,3,4-tetrahydroacridine, generally known by its tradename of Tacrine, has been reported to be useful in the treatment of memory disorders such as Alzheimer's Disease. European Patent application, Publication Nos. 0306825 and 0306826 of 1989, disclose certain N-substituted alkylidine derivatives of Tacrine which are, optionally, also substituted in the acridine ring. Compounds in this category are also mentioned by R. Faure, J. Chim. Phys. Chim. Biol., 78(6) (1981) 527; Khim, Pharm. Zhur., 5(11), (1971) 10–12; Baveja, Ind. J. Pharm. Sci., 48 (1986), 23–25. It has been reported by J. Byrne and T. Acie, British Med. J. 298, (1989) (845) that long term administration of Tacrine is not practical because of hepatotoxicity. More recent studies by Applicants have shown that this problem of hepatotoxicity can be avoided by utilizing purified sources of Tacrine.

$T_4$ lymphocytes are well known to be important cells in the human immunodefense mechanism. Heretofore, reliable methods of increasing $T_4$ levels which have been depressed by disease, have not been available. Stimulating the regeneration of $T_4$ cells therefore, would be a highly desirable achievement. The reduction of opportunistic infections in AIDS patients is a desirable result of stimulating immune responses in such patients. In many cases a reduction $P_{24}$ antigenaemia levels is an indication of such improved responses.

SUMMARY OF THE INVENTION

There are provided pharmaceutical compositions for the elevation of $T_4$ lymphocyte levels in patients having subnormal levels thereof, reducing the level of opportunistic infections in AIDS patients as well as, usually, $P_{24}$ levels and also for inhibiting the activity of the HIV virus in patients which are HIV seropositive but may not exhibit AIDS symptoms, which comprise, as active constituent an effective amount of a compound selected from the group consisting of 9-amino-1,2,3,4-tetrahydroacridine and the acid addition salts thereof with pharmaceutically acceptable acids and a pharmaceutically acceptable carrier. Suitably, the content of active ingredient, ranges from 10 to 300 mg per unit dosage, and may be administered through the parenteral, oral, rectal, percutaneous or permucous routes in the form of tablets, soft gelatine capsules or dragees.

The invention also includes a method of elevating the $T_4$ lymphocyte levels in patients having subnormal levels thereof, reducing the level of opportunistic infections in AIDS patients as well as, usually, $P_{24}$ levels and also for inhibiting the activity of the HIV virus in patients which are HIV seropositive but may not exhibit AIDS symptoms, which comprises administering a safe but effective amount of the active constituent of the above mentioned composition, suitably at a dosage ranges from about 1 to 12 mg/Kg/day.

Compounds which are chemical derivatives of 9-amino-1,2,3,4-tetrahydroacridine but are capable of degradation by human stomach acids, other gastric fluids or intestinal enzymes to 9-amino-1,2,3,4-tetrahydroacridine and have the formula 9-N(Q)-1,2,3,4-tetrahydroacridine, wherein Q is $<$(A.B) where A and B are the same or different and are biologically labile groups are within the scope of the invention, as are compositions containing them and methods of elevating the $T_4$ lymphocyte levels in patients having subnormal levels thereof reducing the level of opportunistic infections in AIDS patients as well as, usually, $P_{24}$ levels and also for inhibiting the activity of the HIV virus in patients which are HIV seropositive but may not exhibit AIDS symptoms, which comprising administering a safe but effective amount of the above mentioned derivatives, suitably at a dosage ranges from about 1 to 12 mg/Kg/day.

Also included in the scope of the invention are pharmaceutical compositions for the elevation of $T_4$ lymphocytes levels in patients having subnormal levels thereof, reducing the level of opportunistic infections in AIDS patients as well as, usually, $P_{24}$ levels and also for inhibiting the activity of the HIV virus in patients which are HIV seropositive but may not exhibit AIDS symptoms, which comprise, as active constituent an effective amount of a compound, capable of degradation by human stomach acids, other gastric fluids or intestinal enzymes to the corresponding 9-amino-1,2,3,4-tetrahydroacridine ring whose homoaromatic is substituted by the moiety X, as well as methods of administering such compounds to patients in need of same suitably at a level of about 1 to 12 mg/Kg/day.

DESCRIPTION OF THE PREFERRED EMBODIMENTS

The present invention is directed to elevating the $T_4$ lymphocyte levels in patients having subnormal levels thereof, reducing the level of opportunistic infections in AIDS patients as well as, usually, $P_{24}$ levels and also for inhibiting the activity of the HIV virus in patients which are HIV seropositive but may not exhibit AIDS symptoms which comprises administering a safe but effective amount of the active constituent. This desired end is achieved by utilizing active constituents which are both old and new and have a close structural relationship to Tacrine (9-amino-1,2,3,4-tetrahydroacridine). Tacrine is an old compound of no known utility in this field.

Certain novel chemical compounds are with the scope of the invention, which are chemical derivatives of 9-amino-1,2,3,4-tetrahydroacridine but are capable of degradation by human stomach acids, other gastric fluids or intestinal enzymes to 9-amino-1,2,3,4-tetrahydroacridine and have the formula 9-N(Q)-1,2,3,4-tetrahydroacridine, wherein Q is $<$(A.B) where A and B are the same or different and are biologically labile groups selected from the group consisting of hydrogen, saturated and unsaturated alkanoyl of 1–20 carbon atoms, naphthyl- and phenyl- saturated and unsaturated alkanoyl of 1–20 carbon atoms in the alkyl moiety, lower alkyl of 1–6 carbon atoms, provided A or B is other than hydrogen.

Among the saturated alkanoyl groups may be mentioned, without limitation, acetyl, propionyl, butyryl, valeryl, decanoyl, dodecanoyl, hexadecanoyl, palmitoyl, and stearoyl. Included in these alkanoyl groups are the acyl moieties of bifunctional acids including, for example, the pimeloyl, sebacoyl, suberoyl, glutaryl and octadioyl moieties. Also included are the 2,6-dichlorobenzoyl, 3,4,5-trimethoxybenzoyl, cinnamoyl, nicotinoyl, isonicotinoyl, furoyl, thienoyl or naphthoyl moieties. As unsaturated alkanoyl moieties, there may be mentioned acryloyl, crotonoyl, fumaroyl, mesaconyl and maleoyl. However, because of the tendency of these groups to polymerize, they are not preferred. Among the alkyl groups, there may be mentioned methyl, ethyl, propyl and isopropyl.

Also within the scope of the invention are compositions, for the elevation of $T_4$ lymphocytes levels in patients having subnormal levels thereof containing pharmaceutically acceptable carriers with, as active constituents derivatives of 9-amino-1,2,3,4-tetrahydroacridine, ring substituted by the moiety X, which are capable of degradation by human stomach acids, other gastric fluids or intestinal enzymes to the active component of these compositions, and have the formula X-[9-N(Q)-amino-1,2,3,4-tetrahydroacridine] wherein Q is $>(A.B)$ or $=CR_3R_4$, wherein A and B are the same or different, and are selected from the group consisting of hydrogen, saturated and unsaturated alkanoyl of 1-20 carbon atoms, naphthyl- and phenyl- saturated and unsaturated alkanoyl of 1-20 carbon atoms in the alkanoyl moiety, lower alkyl of 1-6 carbon atoms, wherein $R_3$ and $R_4$ are lower alkyl of 1-6 carbon atoms substituted and unsubstituted naphthyl and phenyl of 1-3 substituents selected from the group consisting of ($C_1$-$C_6$ alkoxy), ($C_1$-$C_6$ alkanoyl), ($C_1$-$C_6$ dialkyl)amino ($C_1$-$C_6$)alkyl, ($C_1$-$C_6$ alkoxy) ($C_1$-$C_6$ alkyl), halogen, hydroxy, nitro, phenyl, phenylalkyl of 1-6 carbon atoms in the alkyl moiety, phenoxy, amino of the formula $-NR_5.R_6$, wherein $R_5$ and $R_6$ are selected from the group consisting of hydrogen, ($C_1$-$C_6$ alkyl) mercapto, substituted and unsubstituted ($C_1$-$C_6$ alkyl) wherein the substituent is selected from the group consisting of trifluoromethyl, trifluoromethoxy and carboxamido, furoyl, thienyl pyridinyl and pyrrolyl and X is ($C_1$-$C_6$ alkoxy), ($C_1$-$C_6$ alkyl), ($C_1$-$C_6$ alkanoyl), ($C_1$-$C_6$ dialkyl)amino ($C_1$-$C_6$)alkyl, ($C_1$-$C_6$alkoxy) ($C_1$-$C_6$ alkyl), halogen, hydroxy, nitro, phenyl, phenylalkyl of 1-6 carbon atoms in the alkyl moiety, phenoxy, an amino group of the formula $-NR_7.R_8$ wherein $R_7$ and $R_8$ are selected from the group consisting of hydrogen, ($C_1$-$C_6$ alkyl) mercapto, substituted and unsubstituted ($C_1$-$C_6$ alkyl) wherein the substituent is selected from the group consisting of trifluoromethyl, trifluoromethoxy and carboxamido, provided that when Q is $=H_2$, X is other than hydrogen, and the acid addition salts thereof with pharmaceutically acceptable acids. Method of administering said active constituents, suitably at a level of 1-12 mg./kg./day to humans are also within the scope of the invention.

With respect to the foregoing compounds, the definitions of alkyl and alkanoyl as set forth hereinabove.

Hereinabove, the acid additional salts are those of mineral or organic therapeutically compatible acids, for example, such as hydrochlorides, hydrobromides, sulphates, nitrates, phosphates, sulphites, thiosulfates, acetates, butyrates, caproates, suberates, succinates, tartarates, citrates, ascorbates, gluconates, acetoglutarates, glutamates, an aspartates, benzoates, gentisates, silicylates, trimethoxybenzoates, vanillinates, eugenates, nicotinates, naphtoates, benzene sulfonates, methane sulfonates, isothionates, ethane sulfonates, p-toluene sulfonates, camphosulfonates, naphthalene sulfonates, glucose 1-phosphate and glucose 1,6-diphosphate.

Tacrine is a known compound and may be prepared by a process wherein α-anilinonitrile is reacted with cyclohexanone in the presence of a basic catalyst, suitably toluene sulfonic acid, followed by cyclization with lithium isopropyl. In order to produce the corresponding analog substituted in the carboaromatic ring, the appropriately substituted aniline nitrile is utilized as the starting material.

In order to provide the compounds of the present invention wherein A or B (or in the case of bifunctionality, A and B together) are alkanoyl, Tacrine or its appropriate ring substituted analog, is reacted with an acylating agent in the conventional manner, for example, with the corresponding acid halide, acid anhydride or mixed anhydride in the presence of a base, for example, aqueous sodium hydroxide, or by reaction with the appropriate carboxylic acid in the presence of a carbodiimide, such as dicyclohexyl carbodiimide.

Where it is desired to substitute the primary amino group, again this is carried out by conventional procedures in which the desamine Tacrine is converted into the ring halo derivative followed by condensation with the appropriately substituted primary amine.

Where it is desired to produce the corresponding Schiff's Bases, that is to say, those compounds wherein Q is $=CR_5R_6$, is reacted with the appropriate aldehyde or ketone in the presence of a basic organic reagent such as morpholine or piperidine.

The unit doses of pharmaceutical compositions according to this invention contain from 40 to 300 mg. of 9-amino 1,2,3,4-tetrahydroacridine or an addition salt thereof or one of its biological precursors in admixture or conjunction with an inert non-toxic pharmaceutically-acceptable diluent or carrier and preferably from 50 to 200 mg. of active ingredient.

As preferred diluent, there may be mentioned a lecithin such as soya lecithin, or a phospholipid such as a ganglioside or a cerebroside, or a chemically-modified cellulose such as hydroxypropyl methylcellulose.

The pharmaceutical compositions according to this invention which contain as active ingredient, 9-amino tetrahydroacridine, its analogs, metabolic percursors or salts thereof, may be administered through digestive routes such as by means of tablets, coated tablets, microgranules with protected release coatings, dragees, soft gelatine capsules, hard shell capsules, lozenges, potable (oil/water) solutions or suspensions, jellies or emulsions.

For the parenteral administration, there are preferably used solutions or suspensions of the active ingredient put up in ampules, multidose flasks, or auto-injectable syringes. They are preferably utilized in the form of an acid addition salt.

For the purposes of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present inventions are prepared so that a parenteral dosage unit contains between 0.5 to 100 milligrams of active compound.

The solutions or suspensions may also include the following components: a sterile diluent such as water for injection. saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetra acetic acid; buffers such as acetates, citrates or phosphates and agents for the adjustment of tonicity such as sodium chloride or dextrose.

For rectal administration, suppositories or capsules are preferred.

The daily dosage varies, depending on the age of the patients. It may range from 5 to 100 mg. in the children, and from 50 to 600 mg. in the adult man, suitably 1-12 mg/kg/day.

HUMAN CLINICAL TEST RESULTS

Seven Month Follow-Up Study of Tacrine Administration to 26 HIV Infected Patients Protocol Patients had a HIV infection, proved by clinical status and serological tests (Western Blot) and belonged to Stages II, III or IV of CDC classification, but had not received an anti-viral drug (AZT or other) before entering the trial.

Tacrine was supplied as capsules containing 63.5 mg. Tacrine hydrochloride, monohydrate corresponding to 50 mg. base. An inert excipient (lactose) was added to fill white hard size 3 gelatin capsules.

For the first 15 days, patients received 2 capsules a day (i.e., 1 capsule at 8 A.M. and 1 at 8 P.M.). After the first 15 days, if nausea had not occurred or had ceased, the dosage was augmented by 1 capsule (i.e., 1 capsule at 8 A.M., 1 at lunch time and 1 at 8 P.M.). After this second period of 15 days, if nausea had not occurred or had ceased, the dosage was augmented by a further 1 capsule, to reach 4 capsules a day (i.e., 1 capsule at 8 A.M., 1 at lunch time, 1 at 4 P.M. and 1 at 8 P.M.).

Examinations $D_0$—Inclusion Examination—Serological, hematological and clinical determinations. Patients are supplied with capsules of Tacrine for 15 days.

$D_{15}$—First Control after 15 Days Treatment—Serological, hematological and clinical determinations. Patients are supplied with capsules of Tacrine for 15 days.

$D_{1mth}$—Second control after 1 month of Treatment—Serological, hematological and clinical determinations. Patients are supplied with capsules of Tacrine for 1 month.

$D_{n'mth}$—Same as $D_{1mth}$. Following examinations of one month interval each.

Results—Demographic Criteria

Twenty-six patients (25 males and 1 female) were included. Their mean age was 40.3 (range 27-65). CDC classification was: 4 patients stage IVC1; 6 patients stage IVC2; 5 patients stage IVD; 1 patient stage IVE; 5 patients stage III; 5 patients stage II.

Treatment—Dosage

One (1) patient received only 100 mg. a day; 10 patients received 150 mg. a day; 11 patients received 200 mg. a day; 2 patients received 250 mg. a day; 2 patients received 300 mg. a day.

Duration of Treatment

Mean duration of treatment was 6 months.

| | Efficacy - $T_4$ Lymphocytes counts. Evolution (%) in Comparison with $D_0$ | | | | | | | |
|---|---|---|---|---|---|---|---|---|
| $D_0$ value | $D_{15}$ | $D_{1mth}$ | $D_{2mth}$ | $D_{3mth}$ | $D_{4mth}$ | $D_{5mth}$ | $D_{6mth}$ | $D_{7mth}$ |
| 203/mm³ | +5% | +16.7 | +23.9 | +19.5 | +28 | +26.6 | +8.4 | +25.6 |

| | Antigenemia Evolution (%) in Comparison with $D_0$ | | | | | | | |
|---|---|---|---|---|---|---|---|---|
| $D_0$ value | $D_{15}$ | $D_{1mth}$ | $D_{2mth}$ | $D_{3mth}$ | $D_{4mth}$ | $D_{5mth}$ | $D_{6mth}$ | $D_{7mth}$ |
| 462 p g/ml | −38.5 | −35.3 | −22.1 | −24 | −17 | −19.4 | −54 | −51.3 |

| Clinical Status | |
|---|---|
| Mortality: none | |
| Opportunistic infections: | 1 toxoplasmosis |
| (4 cases in 4 patients) | 1 pneumocystosis |
| (4/26 patients) | 2 Kaposi sarcoma emergence |

| Tolerability - Side Effects Incidence | |
|---|---|
| Nausea: | 9 cases (35%) during the first month of treatment. 2 cases (10%) after the first month. |
| Hepatotoxicity: | 0% transaminase elevation. |
| Hematotoxicity: | 0% decrease of hematological counts. |

Withdrawals for Side Effects

Two (2) cases (8%) of severe nausea or neurologic within the first month of treatment.

Seven Month Follow-Up of Tacrine (THA) vs Zidovudine (AZT) in 72 HIV Infected Patients Comparison of serological and clinical status of HIV infected patients after THA versus AZT treatment in an open study.

Method 70 patients (61 males, 11 females) with HIV infection (69 stage IV, 10 stages II and III), received either AZT (46 patients 600–1200 mg./day) or THA (26 patients 150–250 mg/day). In cases of intolerance or inefficacy, treatment was discontinued and patients were treated by the other drug.

Results 13 patients were treated by THA alone, 20 by AZT alone, 26 by AZT then THA and 13 by THA then AZT. Mean duration of treatment was 5.8 months for 53 courses of AZT 5.4 months for 52 courses of THA.

Serological Results

Expressed in mean variation (%) in comparison with $D_o$ values.

| Group | | $D_{1mth}$ | $D_{2mth}$ | $D_{3mth}$ | $D_{4mth}$ | $D_{5mth}$ | $D_{6mth}$ | $D_{7mth}$ |
|---|---|---|---|---|---|---|---|---|
| $T_4/mm^3$ | THA | +20.5 | +31.7 | +55.2 | +74.8 | +91.9 | +52 | +68.3 |
| | AZT | +0.5 | +8.1 | +18.5 | +8.8 | +17.2 | −40 | −40 |
| Agp 24 | THA | −39.4 | −28.3 | −26.2 | −21.5 | −18.7 | −39.5 | −25 |
| | AZT | −20.6 | −3.4 | −1 | +55.6 | +36.5 | +173 | +142 |

| Clinical Results | | | | |
|---|---|---|---|---|
| | Deaths | Opportunistic Infections | Kaposi Emergence | Withdrawals for toxicity |
| AZT (n = 52) | 7 (12%) | 27 (46%) | 3 (5%) | 29 (49%) |
| THA (n = 51) | 0* | 3 (6%) | 2 (4%) | 4 (8%) |

*Significant (p < 0.05) in comparison with AZT courses.

Conclusions

Comparison of THA versus AZT course of treatment shows a decrease in Agp24 levels, mortality and incidences of opportunistic infections after 6 months of treatment. Further studies should be carried out to confirm these results.

Determination of the Inhibitory Action of 9-Amino 1,2,3,4-Tetrahydroacridine (THA) Against RNA Polymerase of HIV Viruses The effect of Tacrine on the activity of the reverse transcriptase of the HIV 1 virus and its effect on the multiplication of the virus on a lymphocytic leukaemic cell line CEM were studied.

Materials and Methods

Cell Culture

The CEM lines utilized for the multiplication of the virus, as well as for the inhibition studies, was provided by Service of Francoise Barre-Sinoussi, at the Institute Pasteur. The culture medium is RPMI 1640, supplemented with 10% fetal calf serum, 2% glutamine and 1% antibiotics. The cells are counted and subcultured in a culture flask every 3 or 4 days. In certain cases, the fungicide amphotericin B is added in dosages of 5 μg./ml.

HIV 1 Virus

The HIV 1 virus was provided from the same source and grown on CEM cells in the culture described above. The infection is created with a supernatant on the culture at a dose level of 50,000 cpm per $10^6$ cells. The infection is followed by the evaluation of the activity of the reverse transcriptase which can reach a level of $10^6$ cpm/ml. at the end of the culture.

For the direct study of the action of the product on the activity of the reverse transcriptase, the virus was concentrated by ultracentrifugation and the plugs of virus removed from the culture medium are resuspended in a solution containing 0.15% Triton X 100, 0.05M Tris at pH 7.8 and 20% glycerol.

These preparations, frozen at −20° C., are active for several months and served for the direct measurement of the products on enzymatic activity.

Measure of the activity of the reverse transcriptase in the supernate of the cultures.

3.6 ml. of the supernatant of cell cultures are ultracentrifuged at 46K rpm for 1 hour in a Sprinco SW 60 rotor. After decantation, the plugs are taken up in 25 μl of a solution containing. 15% of Triton as described above and frozen. For each test, 10 μl of plug solution are utilized.

35 μl of an incubation medium are made up of a solution of 0.07M magnesium chloride, 0.028M potassium chloride, 0.07M Tris at pH 7.8, 1.4 mM DTT and contain 5 μCi of $^3H$ thymidine triphosphate, 2.5 μl of poly A are added to a unit of OD/ml. and 2.5 μl of oligo dT 12-18 to 1 unit of O.D/ml. and finally 10 μl of the plug resuspension from the ultracentrifugation or a control enzymatic preparation. The reaction is carried out in a warm water bath at 37° C. for 1 hour. The incorporated radioactivity which is as precipitated as an acid insoluble form was washed on Millipore HA 0.45 micron filters and counted by liquid scintillation counters.

Action on Reverse Transcriptase of the HIV 1 Virus

The THA is diluted as stated above and added to 40 μl of the incubation solution under a volume of 5.5 μl before the addition of 10 μl of the enzymatic preparation. Initial concentrations of the product are thus 10 times more concentrated than the final dilution in the presence of the enzyme. The controls received 5.5 μl of water.

Several experiments were carried out with THA, the results are all similar and show a 50% inhibition ($Di_{50}$) are attained at a level of 400 μM of product, that is to say, 100 μg/ml.

a) Test Dose of THA

Under the same conditions, there is obtained 50% inhibition with 1 μM of phosphonoformate and with 0.16 U/ml. heparin.

b) Test of THA in Combination with HPA 23 at 4 μg/ml.

The results show that THA gives rise to a synergistic effect with HPA 23 for the inhibition of the HIV 1 reverse transcriptase.

c) Specificity of Action of THA

In order to evaluate the specificity of THA, the effects on the reverse transcriptase and on a non-viral DNA polymerase, namely the polymerase of Micrococcus Lysodecticus have been compared at the same concentrations.

This test shows that the $Di_{50}$ of the THA was at 0.45 mM with respect to the reverse transcriptase and at 1 mM for the inhibition of the DNA polymerase.

Action of the Product on the HIV 1 Infection and the Multiplication of the Virus in CEM Cells Healthy CEM cells were infected with HIV 1 virus at 40,000 cpm per $10^6$ cells. After 7 days of infection at 37° C. an equal quantity of healthy cells are added, non-absorbed viruses removed and $5.10^5$ cells/ml. and 5 ml. of medium are brought into the presence of THA.

During 5 or 6 days, the cells are counted and the supernatant of the culture is recovered for evaluation of the reverse transcriptase activity, that is to say, to determine the production of HIV 1 virus liberated by the cells. The cells are subculture into fresh medium containing the inhibitor at different concentrations.

The results summarized in FIG. 1 show that the viral infection inhibits the proliferation of untreated infected cultures or those treated with 1 μM of THA. At 5 μM, the cells multiply up to the 16th. day and then decline to be destroyed like the previous cultures right up to the 28th day. With 10 μM of THA, the cultures continue to proliferate right up to the 28th day.

Conclusions

THA, at the 5 μM and more particularly at the 10 μM level, protects CEM cultures against the lytic effect of the HIV virus. This effect is found to be dose-dependent. It appears that viral replication persists although significantly diminished with respect to control cultures, in those cultures treated at 5 μM and 10 μM of THA.

The inhibiting effect on reverse transcriptase to inhibit the HIV 1 virus by this mechanism is low. The 50% inhibitory dose ($Di_{50}$) for HIV 1 reverse transcriptase is 500 μM. The protective effect in vivo or in vitro of THA is apparently not due to inhibition of the reverse transcriptase.

Examples of the novel compounds of this invention include:
9-acetylamino-1,2,3,4-tetrahydroacridine;
9-propionylamino-1,2,3,4-tetrahydroacridine;
9-valerylamino-1,2,3,4-tetrahydroacridine;
9-palmitoylamino-1,2,3,4-tetrahydroacridine;
9-pimeloylamino-1,2,3,4-terahydroacridine;
9-glutarylamino-1,2,3,4-tetrahydroacridine;
9-cinnamoylamino-1,2,3,4-tetrahydroacridine;
9-nictinoylamino-1,2,3,4-tetrahydroacridine;
9-methylamino-1,2,3,4-tetrahydroacridamine;
9-isopropylamino-1,2,3,4-tetrahydroacridine;

Examples of the compounds utilized in this invention include:
6-nitro-9-amino-1,2,3,4-tetrahydroacridine;
7-acetyl-9-amino-1,2,3,4-tetrahydroacridine;
8-diethyl-9-amino-1,2,3,4-tetrahydroacridine;
6-phenyl-9-amino-1,2,3,4-tetrahydroacridine;
7-benzyl-9-amino-1,2,3,4-tetrahydroacridine;
8-methoxymethyl-9-amino-1,2,3,4-tetrahydroacridine;

Examples of the compounds utilized in this invention which are disclosed for another use in European Patent publication 0 306 825 include:
N-(phenylmethylene-1,2,3,4-tetrahydro-9-acridinamine;
N-[(4-fluorophenyl)methylene]-1,2,3,4-tetrahydro-9-acridinamine;
N-[(3-fluorophenyl)methylene]-1,2,3,4-tetrahydro-9-acridinamine;
N-[(2-fluorophenyl)methylene]-1,2,3,4-tetrahydro-9-acridinamine;
N-[(2-chlorophenyl)methylene]-1,2,3,4-tetrahydro-9-acridinamine;
N-[(4-chlorophenyl)methylene]-1,2,3,4-tetrahydro-9-acridinamine;
N-[(2,4-dichlorophenyl)methylene]-1,2,3,4-tetrahydro-9-acridinamine;
N-[(4-methoxyphenyl)methylene]-1,2,3,4-tetrahydro-9-acridinamine;
N-[2-thienyl)methylene]-1,2,3,4-tetrahydro-9-acridinamine;
N-[(2-furyl)methylene]-1,2,3,4-tetrahydro-9-acridinamine;
6-chloro-N-(phenylmethylene)-1,2,3,4-tetrahydro-9-acridinamine;
7-chloro-N-(phenylmethylene)-1,2,3,4-tetrahydro-9-acridinamine;
7-methyl-N-(phenylmethylene)-1,2,3,4-tetrahydro-9-acridinamine;
7-methoxy-N-(phenylmethylene)-1,2,3,4-tetrahydro-9-acridinamine;
6-methoxy-N-(phenylmethylene)-1,2,3,4-tetrahydro-9-acridinamine;
6-methyl-N-(phenylmethylene)-1,2,3,4-tetrahydro-9-acridinamine;
7-methyl-N-(phenylmethylene)-1,2,3,4-tetrahydro-9-acridinamine;
6-fluoro-N-(phenylmethylene)-1,2,3,4-tetrahydro-9-acridinamine;
N-[(1-naphthyl)methylene]-1,2,3,4-tetrahydro-9-acridinamine;
N-[(2-naphthyl)methylene]-1,2,3,4-tetrahydro-9-acridinamine;

The foregoing compounds are listed merely for illustration of species of genera and subgenera discussed hereinabove and not for purposes of limitation.

These pharmaceutical compositions are manufactured in accordance with the usual methods of pharmacotechnology. The following examples are intended to illustrate the invention without limiting it in any manner.

EXAMPLE I

Tablets with 100 g. of 9-Amino 1,2,3,4-tetrahydroacridine

| | |
|---|---|
| 9-amino 1,2,3,4-tetrahydroacridine as the hydrated hydrochloride | 117 g. |
| Lactose | 220 g |
| Microcrystalline cellulose | 15 g. |
| Calcium carbonate | 20 g. |
| Calcium phosphate $(PO_4)_2 Ca_3$ | 35 g. |
| Copolymer of ethylene oxide and propylene oxide sold under the Tradename PLURONIC F18 | |
| Magnesium stearate | 15 g. |
| For 1000 tablets, finished at the mean weight of | 0.43 g. |

EXAMPLE II

| Suppositories | |
|---|---|
| Tacrine | 1000 g |
| Cocao butter | 2000 g |

The cocoa butter is melted and the dry powdered Tacrine added thereto and the molten mixture thoroughly mixed in a mixer. The molten composition is then poured into suitable molds to provide 2 gm. suppositories which carry 100 ml. doses of Tacrine.

EXAMPLE III

| Capsules | |
|---|---|
| Tacrine | 100 g. |
| Lactose | 20 g. |
| Talc | 2 g. |

The foregoing components are thoroughly mixed in a powder mixer and then charged to No. 3 gelatin capsules, each of which will contain 100 ml. doses of Tacrine.

EXAMPLE IV

| EXAMPLE IV | |
|---|---|
| Injectable Solution for Intravenous Administration Buffer: | |
| Tris | 0.167 g. |

EXAMPLE IV -continued

| | |
|---|---|
| 0.1 N.Hcl | 4.192 g. |
| Water | 23.3 g. |
| 9-amino 1,2,3,4-tetrahydroacridine (as hydrochloride) | 54 g. |
| Sodium formaldehyde sulfoxylate | 0.5 g. |
| Sodium chloride | 3.7 g. |
| Buffer (as above) | 2.0 g. |
| Total water to | 1000 ml. |

The active ingredient is dissolved into 100 mol. sterile water under clean bacteriological conditions. To the solution, sodium formaldehyde sulfoxylate is added and when dissolved, sodium chloride and tris buffer solution are added thereto.

The whole solution is filtered through porous glass filter and then diluted to the prescribed volume with sterile water.

The solution is divided into ampules of 2 ml. each containing 100 mg. 9-amino-1,2,3,4-tetrahydroacridine for intravenous administration. They are sterilized at 120° C. for 30 min. and are perfectly stable to storage at ambient temperature.

EXAMPLE V

| Solution for slow drip intravenous perfusion | |
|---|---|
| 7-methoxy-9-amino-1,2,3,4-tetrahydroacridine (as the phosphate) | 72.7 g. |
| Glycerol | 1.5 g. |
| Methylparaben | 0.015 g. |
| Isotonic glucose solution to | 1000 ml. |

This solution is prepared in a sterile manner under sterile conditions and packed into plastic envelopes of 1 l capacity.

EXAMPLE VI

| Drinkable Solution | |
|---|---|
| 9-amino-1,2,3,4-tetrahydroacridine (as the ascorbate) | 1.22 g. |
| Glycerol | 4.5 g. |
| Levulose | 20 g. |
| Preservative agent (methylparaben) | 0.015 g. |
| Flavoring agent | q.v. |
| Distilled water to | 100 ml. |

EXAMPLE VII

| Aqueous drinkable suspension | |
|---|---|
| 9-benzylidene amino-1,2,3,4-tetrahydroacridine | 1.35 g. |
| Polyethylene glycol 100 | 0.45 g. |
| Arabic gum | 1.75 g. |
| Sorbitol | 12.5 g. |
| Methylparaben | 0.015 g. |
| Methylcellulose | 2 g. |
| Purified water to | 100 ml. |

EXAMPLE VII(a)

| Coated Tablets | |
|---|---|
| 9-amino 1,2,3,4-Tetrahydroacridine | 75 mg. |
| Silica | 30 mg. |
| Lactose | 164 mg. |
| Carboxymethyl starch as the sodium salt | 9 mg. |
| Talc | 8 mg. |
| Magnesium stearate | 7 mg. |

| Coated Tablets | |
|---|---|
| for a core weighing about 300 mg. | |
| Coating: | Shellac |
| | Gelatine |
| | Arabic Gum |
| | Saccharose |
| | Titanium dioxide |
| | Beeswax |
| | Carnauba wax |
| | Ethyl Vanillin | for a coated tablet finished at an average weight of 300 mg.

The thus-produced cores are introduced into a varnishing turbine and then will be slightly wetted with a concentrated aqueous saccharose solution. Whilst the core are still damp, an alcoholic solution of shellac is sprayed onto for 30 seconds. Once this operation is achieved, a stream of hot air is passed until all ethanol is expelled. When the coated tablets are perfectly dry, an aqueous solution of arabic gum and gelatine previously prepared is sprayed twice on the cores and dried each time. When dry, titanium dioxide, ethylvanillan and talc mixed together are introduced into the surbine by small portions and the whole mixture is rotated until the powders are perfectly incorporated into the tablets.

The tableting is achieved by spraying onto an isopropanolic solution of beeswax and Carnauba wax to give the tablets a shining appearance and a perfectly tough surface.

The tablets have a final average weight of 500 mg.

EXAMPLE VIII

Dermic patches containing about 100 mg. 9-amino 1,2,3,4-tetrahydroacridine per unit A solution of 9-amino 1,2,3,4-tetrahydroacridine as the ascorbate is made by dissolving 50 g. of the said salt into 1000 ml. water. In this solution, precut ribbons of acrylic polymer 50 m. length and 0.30 m. width are immersed for two hours at 37° under a nitrogen atmosphere while avoiding any deformation by mechanical tension. After this period, the ribbon is rolled up on reels, placed in an air-conditioned oven at 37° and fresh air circulated until the humidity content is lower than 5% therein. The thus dried ribbon has a thickness of about 200 μm. It is then coated on both surfaces with an adhesive polymer. One (lower) surface is further covered with a thin protective polyester film which has an upper layer of silicone. This silicone layer prevents any adhesion of the film to the adhesive. Just prior to use, this layer is stripped off and the adhesive contacted to the patient's skin. The other (upper) surface is covered with a colored aluminized polyester coating which insures a protection against loss of active ingredient.

The total thickness of this coated ribbon is of the order of 430–450 μm. The thus assembled ribbons are further cut into square pieces of about 20 cm$^2$ and contain about 100 mg. 9-amino 1,2,3,4-tetrahydroacridine per unit.

EXAMPLE IX

9-Isopropylidene Amino-1,2,3,4-Tetrahydroacridine

In a 3-neck flask fitted with a cooling device, 6.3 g. of 9-amino 1,2,3,4-tetrahydroacridine and 6.9 ml. morpholine were dissolved in 100 ml. acetone and kept under stirring at the reflux temperature for 24 hours. After cooling the solvent was distilled off.

The dry residue was washed with water until neutral and take up in hot methanol. In the cold, the isopropylidenic derivative began to crystallize. After refrigeration overnight, the crystals were suction-filtered, dried, washed with cold water and dried again to yield 9-isopropylideneamino 1,2,3,4-tetrahydroacridine as yellow crystals which melted at 127°–130° C.

EXAMPLE X

9-Methylene amino-1,2,3,4-tetrahydroacridine

A mixture of 8.40 g. 9-amino-1,2,3,4-tetrahydroacridine and 4.71 g. Trioxan in 200 ml. ethanol in which 1 g. triethylamine had previously been dissolved was heated to reflux for 12 hours under vigorous stirring. The mixture was cooled to room temperature, then filtered. The filtrate was concentrated under reduced pressure and the dry residue was taken up in hot acetonitrile (25 ml.). The solution was filtered when hot and then cooled. The methylenic derivative started to crystallize as yellowish crystals.

The compound was purified by recrystallization in a mixture of methanol and after (80:20), the pure compound, yellowing crystals, melted at 140°–142°.

EXAMPLE XI

9-Benzylideneimino-1,2,3,4-tetrahydroacridine

9-Amino-1,2,3,4-tetrahydroacridine (8.27 g.) was refluxed in 300 ml. toluene in which a mixture of 7.0 g. morpholine and 8.4 g. benzaldehyde had previously been admixed. The whole mixture was freshly washed with an aqueous solution of potassium carbonate, dried over sodium sulphate, filtered and refluxed for one night. After cooling, the solvent was distilled off and the oily residue was taken up in 30 ml. methanol, from which the benzylidenic derivative separated as an orange crystalline powder. For analytical purposes, the product was redissolved in toluene and passed through a column of Florisil. Elution with methanol yielded the desired product on evaporation, 13.4 g. as an orange solid which melted at 178°–180°.

EXAMPLE XII

9-Benzoylamino-1,2,3,4-tetrahydroacridine

In a 125 ml. flask, 9.9 g. of 9-amino-1,2,3,4-tetrahydroacridine were dissolved in 60 ml. pyridine. To this solution, 7 g. of benzoyl chloride were added dropwise while maintaining the inner temperature below +5° C. using a water-ice bath. The entire mixture was stirred at this temperature for 3 hours. Excess reagent was destroyed by slowly adding 50 ml. of a saturated aqueous solution of sodium carbonate and stirring for a further hour.

The pyridinic solution was extracted three times with 25 ml. of methylene chloride. The methylenic solutions were combined, washed with water until neutral and dried on sodium sulphate. The solvent was distilled off. The dry residue substantially consisting of 9-benzoylamino-1,2,3,4-tetrahydroacridine was taken up in methanol. On cooling in a refrigerator, the benzoylamino derivative crystallized as colorless plates.

The crystals are then separated, washed with cold methanol then with water and dried. Pure 9-benzoylamino-1,2,3,4-tetrahydroacridine melted at 105°–108°.

In a similar fashion using propionyl chloride instead of benzoyl chloride, 9-propionylamino-1,2,3,4-tetrahydroacridine was obtained.

In a similar fashion using 2,3,5-trimethoxybenzoyl chloride instead of benzoyl chloride, 9-(3,4,5-trimethoxybenzoylamino)-1,2,3,4-tetrahydroacridine was obtained.

EXAMPLE XIII 1,2,3,4-Tetrahydro-9-Butylaminoacridine

Step A:

1,2,3,4-Tetrahydroacridone-9 (1 mol) is added to phosphorous oxychloride (1 mol), followed by phosphorous pentachloride (1.1 mol) and the admixture heated on an oil bath to 120°–130° until evolution of hydrochloric gas was noted (about 15 mn.). The brownish residue which becomes solid on cooling, is poured into iced water. After standing, the green solution is poured into aqueous ammonia and a precipitate of the 9-chloro derivative is given as a crystalline yellow powder which melts at 61°–66°. Upon recrystallization from ethanol, the melting point is increased to 68° C.

Step B:

21.75 g. of 1,2,3,4-tetrahydro-9-chloroacridine are dissolved in 150 ml. dimethyl formamide and the clear solution is added with 29.4 g. butylamine to a closed pressurizable vessel. The mixture is heated to 160° for 12 hours. After cooling, the contents of the vessel are poured into water and the butylamino derivative precipitates. After standing overnight in a cool place, the precipitate is extracted three times with methylene chloride. The organic phases are united, washed with dilute acetic acid, then with water until the washings are neutral. The organic phase is dried then distilled off. The dry residue is taken up in ethanol and the solution is made basic by adding ammonia. 1,2,3,4-tetrahydro-9-butylaminoacridine precipitates as a yellow oil which progressively becomes yellow crystals. The compound is recrystallized from ethyl acetate for the analytical purposes, which melts at about 112° C.

In accordance with the above procedure but where in place of butylamine, there is used methylamine or isopropylamine, there are obtained the corresponding 9-methylamino and 9-isopropylamino-1,2,3,4-tetrahydroacridine.

EXAMPLE XIV

9-Amino 6-nitro,1,2,3,4-tetrahydroacridine

To a stirred solution of cyclohexene-4-one, 1.0 g. 10.0 mmole in methylene chloride (10 ml) at −20° C., a 1M solution of titanium(IV) chloride in methylene chloride (20 ml) was added. The reaction mixture became dark yellow in color and to it a mixture of triethylamine (2.0 g, 20 mmole) 2-amino 6-nitrobenzonitrile (1.2 g, 10.0 mmole) in methylene chloride (30 ml) were added. The reaction mixture immediately became dark in color and was allowed to warm to room temperature (about 25° C.) and stirred further for 15 hours. At the end of this period, the reaction mixture was treated with 25% aqueous NaOH (40 ml) and methylene chloride (100 ml) and was filtered through a 2 inch diatomaceous earth pad (Celite Trademark) which was washed with methylene chloride (50 ml) and water (100 ml). The organic layer was separated, washed once with water (30 ml) and dried (anhydrous MgSO$_4$). The methylene chloride was removed under vacuum to afford an oil which was triturated with ether to give the title compound.

In accordance with the above procedure but in place of 2-amino-6-nitrobenzonitrile, the corresponding 2-6-phenylbenzonitrile is used, the corresponding 9-amino-5-phenyl,1,2,3,4-tetrahydroacridine is obtained.

We claim:

1. A method of the alleviation of the symptoms of Acquired Immunodeficiency Syndrome (AIDS) in patients having the same which comprises administering to said patient an effective amount of an acridinamine compound selected from the group consisting of 9-amino-1,2,3,4-tetrahydroacridine and the acid addition salts thereof with pharmaceutically acceptable acids.

2. The method of claim 1 wherein the effective amount ranges from about 1 to 12 mg/Kg/day.

3. The method of claim 1 wherein said administration is provided in conjunction with administration of an antiviral drug.

4. The method of claim 3 wherein the said antiviral drug is selected from the group consisting of derivatives of thymidine, uracil and uridine.

5. The method of claim 3 wherein the said antiviral drug is selected from the group consisting of AZT and DDI.

6. The method of claim 3 wherein the effective amount ranges from about 1 to 12 mg/Kg/day of the acridinamine in conjunction with dosage ranges from about 2 to 24 mg/Kg/day of AZT or DDI.

7. A method of reducing the HIV viral levels in a HIV seropositive patient which comprises administering to said patient an effective amount of a compound selected from the group consisting of 9-amino-1,2,3,4-tetrahydroacridine and the acid addition salts thereof with pharmaceutically acceptable acids.

8. A method of elevating the $T_4$ lymphocyte levels in a patient having subnormal levels thereof which comprises administering to said patient an effective amount of of a compound selected from the group consisting of 9-amino-1,2,3,4-tetrahydroacridine and the acid addition salts thereof with pharmaceutically acceptable acids.

9. A method of reducing $P_{24}$ antigenaemia titre levels in a patient having excess levels thereof which comprises administering to said patient an effective amount of a compound selected from the group consisting of 9-amino-1,2,3,4-tetrahydroacridine and the acid addition salts thereof with pharmaceutically acceptable acids.

* * * * *